US007652152B2

(12) United States Patent
Roh et al.

(10) Patent No.: US 7,652,152 B2
(45) Date of Patent: Jan. 26, 2010

(54) SYNTHETIC METHOD OF OPTICALLY PURE (S)-3-HYDROXYPYRROLIDINE

(75) Inventors: Kyoung Rok Roh, Daejeon (KR); Ji Sang Yoo, Daejeon (KR); Jong Won Jang, Daejeon (KR); Dae Yon Lee, Daejeon (KR)

(73) Assignee: Chiroad Incorporate, Daejeon (KR)

( * ) Notice: Subject to any disclaimer, the term of this patent is extended or adjusted under 35 U.S.C. 154(b) by 128 days.

(21) Appl. No.: 11/996,011

(22) PCT Filed: Jul. 19, 2006

(86) PCT No.: PCT/KR2006/002835

§ 371 (c)(1),
(2), (4) Date: Jan. 17, 2008

(87) PCT Pub. No.: WO2007/011162

PCT Pub. Date: Jan. 25, 2007

(65) Prior Publication Data

US 2008/0214837 A1    Sep. 4, 2008

(30) Foreign Application Priority Data

Jul. 20, 2005    (KR) .................. 10-2005-0065698

(51) Int. Cl.
*C07D 207/12*    (2006.01)
(52) U.S. Cl. .................................................. 548/541
(58) Field of Classification Search .................. None
See application file for complete search history.

(56) References Cited

U.S. PATENT DOCUMENTS

| 4,910,320 | A | * | 3/1990 | Inoue et al. ................. 548/541 |
| 4,916,141 | A |   | 4/1990 | Sanchez |
| 5,179,212 | A | * | 1/1993 | Takahashi et al. ........... 548/541 |

FOREIGN PATENT DOCUMENTS

| EP | 0 160 451 A | 11/1985 |
| EP | 0 304 087 A | 2/1989 |
| EP | 0 347 810 A | 12/1989 |
| EP | 0 366 327 A | 5/1990 |
| EP | 0 391 169 A | 10/1990 |
| EP | 0 398 726 A | 11/1990 |
| EP | 0 431 521 A | 6/1991 |
| JP | 57-56457 | 4/1982 |
| JP | 60-104061 | 6/1985 |
| JP | 61-63652 | 4/1986 |
| JP | 61-267577 | 11/1986 |
| JP | 5-255204 | 10/1993 |
| JP | 2001-220372 | 8/2001 |
| WO | WO 88/08845 | 11/1988 |
| WO | WO 97/40008 | 10/1997 |
| WO | WO 97/43256 | 11/1997 |
| WO | WO 00/15610 | 3/2000 |
| WO | WO 01/19817 | 3/2001 |
| WO | WO 03/097594 | 11/2003 |

OTHER PUBLICATIONS

Naylor, Alan et al.: "4-[(Alkylamino)methyl]furo[3,2-c]pyridines: A New Series of Selective k-Receptor Agonists", *J. Med. Chem.*, 1994, 37, pp. 2138-2144.

Volkmann, Robert A. et al.: "2-Thioalkyl Penems : An Efficient Synthesis of Sulopenem, a (5R,6S)-6-(1(R)-Hydroxyethyl)-2-[(cis-1-oxo-3-thiolanyl)thio]- 2-penem Antibacterial", *J. Org. Chem.*, 1992, 57, pp. 4352-4361.

Tamazawa, Kazuharu et al.: "Stereoselectivity of a Potent Calcium Antagonist, 1-Benzyl-3-pyrrolidinyl Methyl 2,6-Dimethyl-4-(m-nitrophenyl)-1,4-dihydropyridine-3,5-dicarboxylate", *J. Med. Chem.*, 1986, 29, pp. 2504-2511.

Trybulski, Eugene J.: "The Synthesis and Structure Activity Relationships of Enantiomerically Pure Hydroxylated Oxotremorine Derivatives", *Bioorganic & Medical Chemistry Letters*, vol. 2, No. 8, 1992, pp. 827-832.

Mehler, Thomas et al.: "Enantioselective Addition of Diethylzinc to Aromatic Aldehydes Catalysed by Chiral Ligands Derived from L-Hydroxyproline", *Synthetic Communications*, 23(19), 1993, pp. 2691-2699.

Houghton, Peter G. et al.: "Enantiospecific Synthesis of the (4R)-1-Azabicyclo[2.2.1]heptane Ring System", *J. Chem. Soc. Perkin Trans I*, 1993, pp. 1421-1424.

Rhee, Jaekeol et al.: "Synthesis of Some Carbapenem Derivatives and their Antibacterial Activities", *Korean J. of Med. Chem.*, vol. 3, No. 1, 1993, pp. 72-80.

Giardina, Giuseppe et al.: Facile and Efficient Syntheses of Novel (s)- and (R)-3-Fluropyrrolidines and 3,3-Difluoropyrrolidine, *Synlett*, Jan. 1995, pp. 55-57.

Wallbaum, Sabine et al.: Decarboxylation of α-Amino Acids Containing Two and Three Stereogenic Centers : A Simple One-Step Procedure to Prepare Two Optically Active β-Amino Alcohols and a Bicyclic Pyrrolidine Derivative, *Synthetic Communications*, 24 (10), 1994, pp. 1381-1387.

(Continued)

*Primary Examiner*—Fiona T Powers
(74) *Attorney, Agent, or Firm*—Frommer Lawrence & Haug LLP; Ronald R. Santucci

(57) ABSTRACT

A method of preparing optically pure (S)-3-hydroxypyrrolidine is disclosed. The present invention provides a method of economically and industrially preparing optically and chemically pure (S)-3-hydroxypyrrolidine, through a process comprising introducing an amine protecting group by using optically pure 4-amino-(S)-2-hydroxybutylic acid as a starting material, reducing a carboxylic acid group into a primary alcohol, removing the amine protecting group to form an amine salt, halogenating the primary alcohol, and amine cyclization; and through a simple purification process, i.e., distillation under reduced pressure. As another method, the present invention provides a method of preparing optically and chemically pure (S)-3-hydroxypyrrolidine, through a process comprising esterifying optically pure 4-amino-(S)-2-hydroxybutylic acid as a starting material, lactam cyclization, and reduction.

15 Claims, No Drawings

OTHER PUBLICATIONS

Bhat, Krishna L. et al.: "Synthetic Routes to Chiral 3-Pyrrolidinols", *Synthetic Communications*, 15(7), 1985, pp. 587-598.

Shibata, Tomoyuki et al.: "Synthesis of Optically Active 3-Mercaptopyrrolidine Derivatives, Synthetic Intermediates of Carbapenem RS-533 and its Isomer", *Heterocycles*, vol. 24, No. 5, 1986, pp. 1331-1346.

Yoshida, Akira et al.: "An Efficient Carbapenem Synthesis via an Intramolecular Wittig Reaction of New Trialkoxyphosphorane-Thiolesters", *Tetrahedron Letters*, vol. 25, No. 26, 1984, pp. 2793-2796.

Harris, Bruce D., et al.: "Synthesis of 3S-Pyrrolidinol from L-Glutamic Acid", *Synthetic Communications*, 16(14), 1986, pp. 1815-1822.

* cited by examiner

SYNTHETIC METHOD OF OPTICALLY PURE (S)-3-HYDROXYPYRROLIDINE

This application is a 371 of PCT/KR2006/002835 filed on Jul. 19, 2006, published on Jan. 25, 2007 under publication number WO 2007/011162 A1 which claims priority benefits from South Korean Patent Application Number 10-2005-0065698 filed Jul. 20, 2005, the disclosure of which is hereby incorporated by reference.

TECHNICAL FIELD

The present invention relates to a method of preparing optically pure (S)-3-hydroxypyrrolidine, and more particularly, to a simple and economical method of preparing optically and chemically pure (S)-3-hydroxypyrrolidine through an economical and industrial process and a simple purification process, i.e., distillation under reduced pressure, by using optically pure 4-amino-(S)-2-hydroxybutylic acid as a starting material.

BACKGROUND ART (S)-3-hydroxypyrrolidine represented by the following Formula 1 is a very important compound in preparing pharmaceutical products, which has been widely used as a major chiral intermediate for pharmaceutical products commercially available on the market and new pharmaceutical products under clinical tests, and thus, there have been many studies thereon.

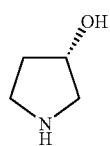

<Formula 1>

Examples in which (S)-3-hydroxypyrrolidine represented by Formula 1 are actually used in preparing pharmaceutical products are as follows: a major intermediate raw material of a calcium antagonist (Barnidipine) (European Patent Laid-Open Publication No. 160,451; J. Med. Chem. 1986, 29, 2504~2511; Japanese Patent Laid-Open Publication No. (Sho) 61-267577; Japanese Patent Laid-Open Publication No. (Sho) 61-63652); carbapenem antibiotics (Heterocycles, vol 24, No 5, 1986; Tetrahedron Lett., 25, 2793, 1984; International Publication No. WO88/08845; J. Org. Chem. 1992, 57, 4352~4361); quinolone-based antibiotics (U.S. Pat. No. 4,916,141; European Patent Laid-Open Publication No. 391, 169; European Patent laid-Open Publication No. 304,087), analgesics (κ-receptor agonists) (European Patent Laid-Open Publication Nos. 398,720 and 366,327; J. Med. Chem., 1994, 37, 2138~2144), and a major intermediate raw material of a neurotransmitter (International Publication No. WO01/19817). That is, (S)-3-hydroxypyrrolidine is used as a major substance for preparation of various chiral pharmaceutical products in a wide range of application fields.

Conventional techniques related to preparation of optically pure (S)-3-hydroxypyrrolidine, which is useful as a major intermediate for preparation of chiral compounds described above, will be described below.

For example, a method of preparing 3-(R)-hydroxypyrrolidine in a single step reaction involving decarboxylation using (R)-3-hydroxy-L-proline as a starting material is disclosed (JP2001220372; WO97/43256; JP05255204; Synlett, 1995, 55-57; Syn. Comm. 1994, 24, 1381~1387; Korean J. of Med. Chem. 1993, 3, 72~80; Syn. Comm. 1993, 23, 2691~2699; J. Chem. Soc. Perkin Trans. 1. 1993, 1421~1424; Bioorganic & Medicinal Chemistry Letters, 2, 827). However, in case of 3-(R)-hydroxypyrrolidine, the starting material, (R)-3-hydroxy-L-proline, is very expensive and thus is difficult to be applied to mass production.

A method of obtaining (S)-3-hydroxypyrrolidine through several steps using D-malic acid as a raw material is known (Syn. Commun. 15, 587~598, 1985; J. Med. Chem. 1994, 37, 2138~2144). However, this technique has a disadvantage of multiple steps being involved and also has problems in that LiAlH4 or B2H6 used as a reduction agent is expensive and difficult to industrially handle. Further, since D-malic acid is expensive and is not mass-produced, this method is not an economical preparation method.

Recently, a new synthetic method that comprises an epoxy ring-opening reaction by way of amine of 3,4-epoxy-1-butanol followed by 5-cyclization (WO2003/097594) has been reported. However, this method has a disadvantage in that raw materials are expensive. Further, synthesis of (S)-3-hydroxypyrrolidine and derivatives thereof through activation of a hydroxyl group followed by double substitution of amine, by using 1,2,4-trihydroxybutane, which is a derivative of 3,4-epoxy-1-butanol, as a starting material has been reported (WO2000/015610). However, this method also suffers from a problem that raw materials are expensive.

As for similar methods, there has been known a synthetic method using a derivative of a 3,4-dihydroxy-1-butanol (JP60104061); a synthetic method using 3,4-dihydroxy-1-butylamine (JP57056457); and a synthetic method comprising cyan group substitution and cyan group reduction followed by cyclization, using 3-chloro-1,2-propandiol and derivatives thereof (EP431,521 and EP347,818). However, these preparation methods also have a problem in that it is difficult to industrially supply raw materials.

Therefore, there is a need for development of a method of preparing (S)-3-hydroxypyrrolidine using an inexpensive, optically active raw material as a starting material so that it can be industrially mass-produced.

DISCLOSURE OF INVENTION

Technical Problem

The present invention is conceived to solve the aforementioned problems. It is an object of the present invention to provide a method of industrially and economically preparing (S)-3-hydroxypyrrolidine by using inexpensive, optically active 4-amino-(S)-2-hydroxybutylic acid as a starting material, and a method of optically or chemically purifying (S)-3-hydroxypyrrolidine through simple distillation under reduced pressure without an additional purification process.

Technical Solution

The present invention for achieving these objects has the following features.

In one general aspect, a method of preparing (S)-3-hydroxypyrrolidine according to the present invention comprises the steps of: introducing an amine protecting group into an amine group of optically pure 4-amino-(S)-2-hydroxybutylic acid represented by the following Formula 2 used as a starting material; reducing a carboxylic acid group into a primary alcohol; removing the amine protecting group to form an amine salt; halogenating the primary alcohol to perform activation into a leaving group; and synthesizing optically pure (S)-3-hydroxypyrrolidine represented by the following Formula 1 through amine cyclization:

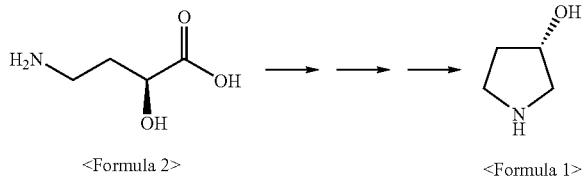

<Formula 2>  <Formula 1>

Further, a compound prepared in the step of forming the amine protecting group in the amine group of 4-amino-(S)-2-hydroxybutylic acid may comprise a compound represented by the following Formula 3:

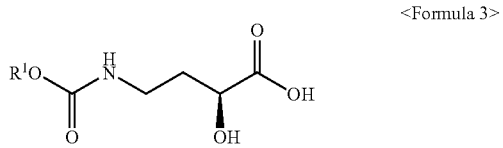

<Formula 3> where $R^1$ is a $C_1$~$C_{12}$ linear or branched alkyl or benzyl group.

Moreover, the step of reducing the carboxylic acid group to the primary alcohol may be performed by esterifying the carboxylic acid group into an ester compound represented by the following Formula 4 and reducing an ester group to the primary alcohol:

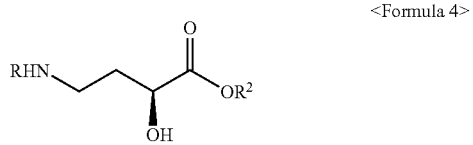

<Formula 4> where R is an amine protecting group, and $R^2$ is a $C_1$~$C_{12}$ linear or branched alkyl or benzyl group.

Furthermore, a compound prepared in the step of removing the amine protecting group to form the amine salt may comprise a compound represented by the following Formula 5:

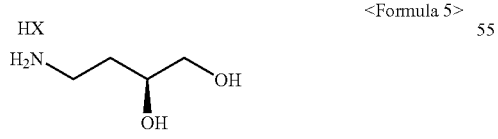

<Formula 5> where HX is halogen acid or sulfuric acid.

In addition, a compound prepared in the step of halogenating the primary alcohol to perform activation into the leaving group may comprise a compound represented by the following Formula 6:

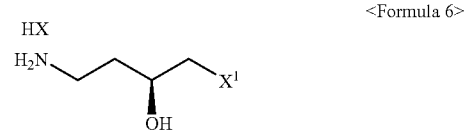

<Formula 6> where HX is halogen acid or sulfuric acid, and $X^1$ is halogen.

Further, the step of forming the amine protecting group in the amine group of 4-amino-(S)-2-hydroxybutylic acid may employ at least one reaction solvent selected from the group consisting of water, 1,4-dioxane, tetrahydrofuran and acetonitrile.

Moreover, the step of halogenating the primary alcohol to perform activation into the leaving group may use bromic acid and acetic acid, anhydride bromic acid or acetylbromide when the primary alcohol is brominated.

Furthermore, the step of halogenating the primary alcohol to perform activation into a leaving group may be performed at a reaction temperature ranging from 0 to 100° C. by using a $C_1$~$C_4$ liquid alkyl solvent with a carboxylic acid group as a reaction solvent.

In addition, the step of synthesizing optically pure (S)-3-hydroxypyrrolidine through the amine cyclization may be performed by using water, $C_1$~$C_4$ linear or branched alcohol, or a mixture thereof as a reaction solvent, and $Na_2CO_3$, $K_2CO_3$, $NaHCO_3$, LiOH, NaOH, KOH, $Ca(OH)_2$ or TEA as a base.

In another general aspect, a method of preparing (S)-3-hydroxypyrrolidine according to the present invention comprises the steps of: forming an ester compound by esterifying a carboxylic acid group of optically pure 4-amino-(S)-2-hydroxybutylic acid represented by the following Formula 2 used as a starting material; forming a lactam compound through lactam cyclization of the ester compound; and synthesizing optically pure (S)-3-hydroxypyrrolidine represented by the following Formula 1 through amide reduction of the lactam compound:

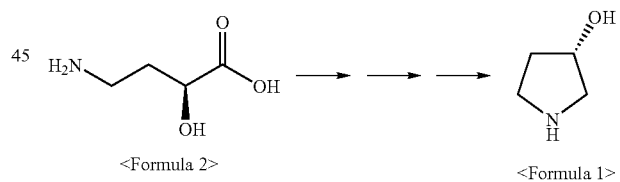

<Formula 2>  <Formula 1>

Further, the ester compound may comprise a compound represented by the following Formula 7:

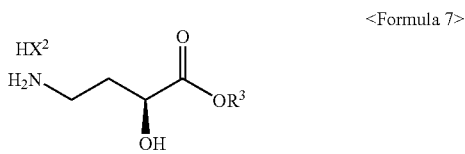

<Formula 7> where $R^3$ is a $C_1$~$C_{12}$ linear or branched alkyl or benzyl group, and $HX^2$ is halogen acid or sulfuric acid.

Moreover, the step of preparing the ester compound by esterifying the carboxylic acid group of optically pure 4-amino-(S)-2-hydroxybutylic acid may employ a base selected from the group consisting of sodium carbonate, potassium carbonate, sodium bicarbonate, potassium hydroxide, sodium hydroxide and a tertiary alcohol.

*Furthermore, the step of synthesizing optically pure (S)-3-hydroxypyrrolidine through the amide reduction of the lactam compound may use diglym as a reaction solvent.

In addition, the step of synthesizing optically pure (S)-3-hydroxypyrrolidine through the amide reduction of the lactam compound may be performed at a reaction temperature of 20 to 150° C. by using 1 to 10 equivalents of sodium borohydride as a reducing agent and 1 to 4 equivalents of sulfuric acid based on the lactam compound.

ADVANTAGEOUS EFFECTS

As described above, the present invention provides a method capable of economically and industrially preparing (S)-3-hydroxypyrrolidine by using inexpensive, optically active 4-amino-(S)-2-hydroxybutylic acid as a starting material, and preparing optically and chemically pure (S)-3-hydroxypyrrolidine through simple distillation under reduced pressure without an additional purification process.

BEST MODE FOR CARRYING OUT THE INVENTION

Hereinafter, the present invention will be described in greater detail.

*The present invention provides a method of preparing optically and chemically pure (S)-3-hydroxypyrrolidine, which employs a process of the following Reaction Scheme 1 using 4-amino-(S)-2-hydroxybutylic acid as a starting material, or a mild reaction condition of Reaction Scheme 2 (to be described later) and a simple purification process.

First, the method of preparing (S)-3-hydroxypyrrolidine by using 4-amino-(S)-2-hydroxybutylic acid as a starting material according to the process of Reaction Scheme 1 will be described as follows:

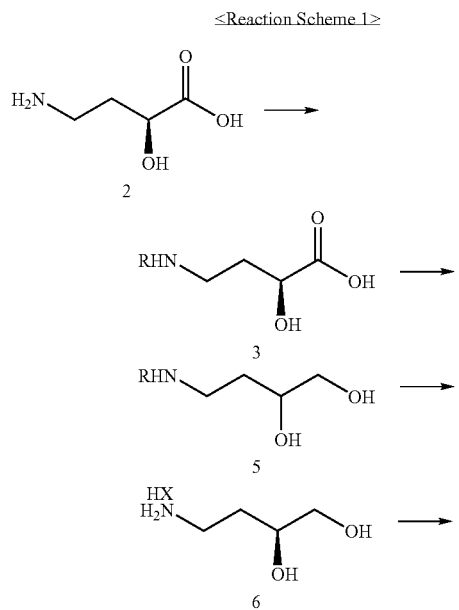

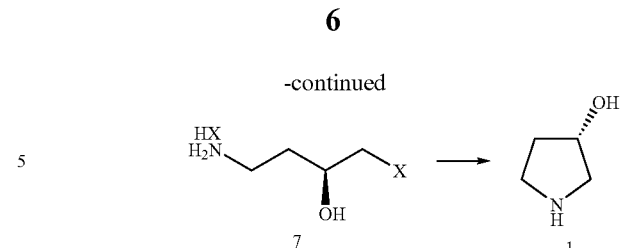

As shown in Reaction Scheme 1, the present invention provides a method of preparing (S)-3-hydroxypyrrolidine, which comprises the steps of: 1) introducing an amine protecting group into a compound 2 to obtain a compound 3; 2) reducing a carboxylic acid group of the compound 3 to a primary alcohol to obtain a compound 5; 3) removing the amine protecting group from the compound 5 to obtain an amine salt 6; 4) halogenating the primary alcohol of the amine salt 6 to obtain a compound 7 having an activated leaving group; and 5) performing amine cyclization of the compound 7 to obtain (S)-3-hydroxypyrrolidine 1.

The step of introducing an amine protecting group into a compound 2 can be achieved by introducing an amine protecting group through amidation or carbamation conventionally used in the art. Specifically, the amine protecting group can be introduced in the form of amide by using $C_1$~$C_{12}$ aliphatic or aromatic alkylcarboxyl halide (or a leaving group such as an ester). Further, it is also possible to introduce the amine protecting group in the form of phthalimide by using phthalic anhydride. However, it is desirable to introduce the amine protecting group by using $C_1$~$C_{12}$ linear or branched alkyl or benzyl chloroformate (or chloride may be replaced by a leaving group such as halogen or alkoxy) to obtain the following compound 3a:

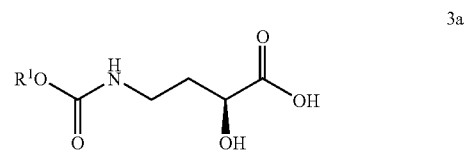

where $R^1$ is preferably a $C_1$~$C_{12}$ linear or branched alkyl or benzyl group.

There is no limitation on a reaction solvent, but it is desirable to select the reaction solvent from the group consisting of water, 1,4-dioxane, tetrahydrofuran, acetonitrile and a mixture thereof.

Sequentially, the step of preparing a compound 5 by reducing the carboxylic acid group of the compound 3 to a primary alcohol can be performed through a process of directly reducing a carboxylic acid group to a primary alcohol, which is known in the art, without any limitation. Reducing agents useful in the step include sodium borohydride (BH3)(JACS, 92, 1637, 1970; JOC 38, 2786, 1973), 9-BBN (JOC, 42, 512, 1977), sodium borohydride under the presence of a catalyst (JACS 78, 2582, 1956; Syn 695, 1980), lithium aluminum hydride (JACS, 109, 7816, 1987), and the like. Since details of the reduction methods can be found in these references, further description thereof will be omitted herein.

As for a preferred reduction method enabling a higher yield and industrial mass production, the carboxylic acid group of the compound 3 is subjected to esterification to obtain the following ester compound, and the ester group of the compound 4 is then reduced to obtain the compound 5. The esterification may be performed by means of esterification of a carboxylic acid, which is known in the art, without any limitation.

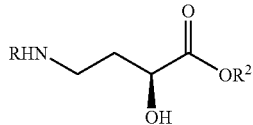

where it is preferred that R be an amine protecting group, and $R^2$ be a $C_1$~$C_{12}$ linear or branched alkyl or benzyl group.

The reduction of the ester compound 4 may be performed by means of reduction of an ester group into an alcohol, which is known in the art, without any limitation. Preferably, the reduction is carried out by using sodium borohydride as a reducing agent in an amount of 1 to 10 equivalents, more preferably 2 to 5 equivalents.

Next, the step of preparing the amine salt 6 by removing the amine protecting group from the compound 5 can be achieved by removing the amine protecting group through agitation with or without reflux after addition of an acid such as halogen acid or sulfuric acid thereto. Sometimes, it is possible to form the amine salt 6 by removing the amine protecting group through addition of a base or hydrazine and adding a large quantity of acid thereto. It is most preferable to use bromic acid.

Sequentially, in the step of preparing the compound 7 having an activated leaving group by halogenating the primary alcohol of the amine salt 6, the primary alcohol should be selectively halogenated. To this end, the selective activation of the primary alcohol in the present invention can be achieved by the halogenation.

In case of performing the halogenation, all kinds of halogenating agents generally known in the art can be used, but it is preferable to perform bromination in view of reactivity by using, as a brominating agent, anhydride bromic acid, more preferably acetylbromide and bromic acid/acetic acid. In this case, an intermediate with an acetylated secondary alcohol is first synthesized, and a target substance with a brominated primary alcohol can be obtained by reacting the intermediate with an alcohol at an elevated temperature. It is preferable to employ a liquid compound having a $C_1$~$C_4$ alkylcarboxylic acid group as a reaction solvent, more preferably an acetic acid. This is carried out at a reaction temperature ranging from 0 to 100° C., preferably 10 to 50° C. for 1 to 24 hours, preferably for 3 to 6 hours.

Next, the step of preparing (S)-3-hydroxypyrrolidine 1 through amine cyclization of the compound 7 uses a reaction solvent selected from the group consisting of water, a $C_1$~$C_4$ linear or branched alcohol and a mixture thereof, and a base selected from the group consisting of $Na_2CO_3$, $K_2CO_3$, $NaHCO_3$, LiOH, NaOH, KOH, $Ca(OH)_2$ and TEA.

After the reactions are completed, the resulting reaction mixture is concentrated under reduced pressure to remove the solvent, and the concentrate thus obtained is then subjected to distillation under reduced pressure, thereby easily obtaining chemically and optically pure (S)-3-hydroxypyrrolidine 1.

The amine cyclization may be carried out in succession to the step of preparing the compound 7 with an activated leaving group by halogenating the primary alcohol of the amine salt 6.

The method of the following Reaction Scheme 2 as another method of the present invention is a method of preparing chemically and optically pure (S)-3-hydroxypyrrolidine under a mild reaction condition and through a simple purification process by using 4-amino-(S)-2-hydroxybutylic acid as a starting material.

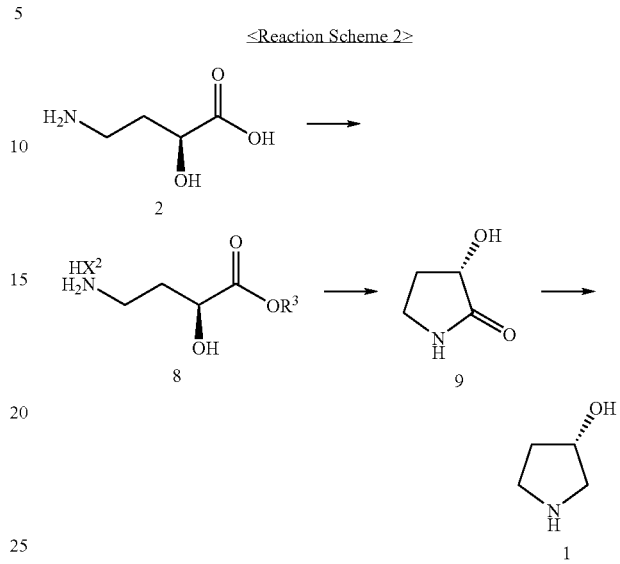

where it is preferred that $R^3$ be a $C_1$~$C_{12}$ linear or branched alkyl or benzyl group, and $HX^2$ be halogen acid, sulfuric acid or fatty acid.

As illustrated in Reaction Scheme 2, the present invention provides a method of preparing (S)-3-hydroxypyrrolidine 1, which comprises the steps of: 1) esterifying a carboxylic acid group of a starting material 2 to obtain an ester compound 8; 2) forming a lactam compound 9 through lactam cyclization of the ester compound 8; and 3) reducing a carbonyl group of the lactam compound 9 through amide reduction. The esterification and lactam cyclization mentioned above may be subjected to a purification process in each of the steps but are preferably performed consecutively without any purification process.

In the step of preparing the ester compound 8 by esterifying the carboxylic acid group of the starting material 2, a $C_1$~$C_{12}$ linear or branched alkyl or benzyl alcohol is added to the starting material, an acidic condition is made by adding 1 to 10 equivalents, preferably 1 to 2 equivalents of halogen acid, sulfuric acid or an organic acid, and then, the mixture is reacted at a temperature of 0 to 150° C. (or reflux condition) under the acidic condition. At this time, there is no limitation on a solvent, but it is preferable to employ a $C_1$~$C_{12}$ linear or branched alkyl or benzyl alcohol as a solvent.

The step of forming the lactam compound 9 through lactam cyclization of the ester compound 8 may be subjected to an additional purification process after the step of preparing the ester compound 8 by esterifying the carboxylic acid group of the starting material 2. However, it is more desirable to consecutively perform these steps.

There is no limitation on a base to be used, but it is preferable to employ sodium carbonate, potassium carbonate, sodium bicarbonate, potassium hydroxide, sodium hydroxide, or a linear or branched tertiary alkylamine with identical or different $C_1$~$C_4$ side chains. Further, the reaction solvent include, but is not limited to, water, an alcohol and the like, and it is preferable to use the same solvent as used for the preparation of the compound 8.

Next, in the step of reducing the carbonyl group of the lactam compound 9 through amide reduction, it is preferable to use diglym as the reaction solvent and the reaction is performed by using 1 to 10 equivalents, preferably 2 to 5 equivalents of sodium borohydride and 2 to 4 equivalents of sulfuric acid at a reaction temperature of 20 to 150° C., preferably 70 to 100° C. After the reaction is completed, the resulting reaction mixture is treated at pH 7 or more, concentrated under reduced pressure to remove the solvent, and then subjected to distillation under reduced pressure, thereby easily obtaining chemically and optically pure (S)-3-hydroxypyrrolidine 1.

Hereinafter, the present invention will be described in greater detail in connection with examples. The following examples are given for the purpose of illustration and should not be constructed as limiting the scope of the invention. It will be apparent that other examples of the present invention can be easily conceived by those skilled in the art from the examples described herein and fall within the scope of the invention.

EXAMPLE 1

Preparation of
4-ethoxycarbonylamino-(S)-2-hydroxybutylic acid 3

Distilled water (150☐) and 4-amino-(S)-2-hydroxybutylic acid 2 (0.84 mol, 100 g), and sodium hydroxide (1.68 mol, 67 g) were added to a 1000☐ round-bottom flask and completely dissolved. The mixture was cooled down below 5° C. After a solution prepared by dissolving ethyl chloroformate (1.00 mol, 109 g) in 1,4-dioxane (100☐) was gently dropped to the cooled mixture, the resulting mixture was agitated for 2 hours while maintaining reaction temperature at room temperature. The completion of the reaction was confirmed by TLC. The reaction mixture was concentrated under reduced pressure and cooled down to 10° C., and then, its pH was lowered to 1.2 or less by adding concentrated hydrochloric acid. The resulting mixture was extracted with ethyl acetate (450☐), and the extract thus obtained was dried with anhydrous magnesium sulfate and then filtered and concentrated to obtain 153 g of 4-ethoxycarbonylamino-(S)-2-hydroxybutylic acid 3.

$^1$H-NMR (D$_2$O): δ 4.05-4.22 (m, 1H), 3.83-3.95 (m, 2H), 3.15 (t, 2H, J=10.5 Hz), 1.7-2.0 (m, 2H), 1.0-1.2 (m, 3H).

EXAMPLE 2

Preparation of
4-ethoxycarbonylamino-(S)-2-hydroxybutylic acid
ethylester 4

After 4-ethoxycarbonylamino-(S)-2-hydroxybutylic acid 3 (0.523 mol, 100 g) and 240☐ of anhydrous alcohol were added to a 500☐ round-bottom flask and completely dissolved, 5 g of concentrated sulfuric acid was gradually dropped thereto. The mixture was reacted under reflux for 10 hours. After the reaction was completed, the reaction mixture was cooled down to room temperature, neutralized with sodium bicarbonate, and then concentrated under reduced pressure to obtain 110 g of crude 4-ethoxycarbonylamino-(S)-2-hydroxybutylic acid ethylester 4.

$^1$H-NMR (DMSO-d$_6$): δ 4.03-4.2 (m, 3H), 3.9-4.0 (m, 2H), 3.03 (m, 2H), 1.2-2.0 (m, 2H), 1.0-1.2 (m, 6H).

EXAMPLE 3

Preparation of
4-ethoxycarbonylamino-(S)-1,2-butandiol 5

Sodium borohydride (1.00 mol, 37.8 g) and 200☐ of anhydrous ethanol were added to a 1000☐ round-bottom flask, and reaction temperature was lowered to 5° C. While carefully maintaining the reaction temperature below 15° C., a solution prepared by dissolving 4-ethoxycarbonylamino-(S)-2-hydroxybutylic acid ethylester 4 (0.502 mol, 110 g) in 240☐ of anhydrous ethanol was gradually added to the mixture. The reaction mixture was agitated for 6 hours while maintaining the reaction temperature at 20° C. After the completion of the reaction was confirmed, the reaction mixture was cooled down and kept below 5° C. The reaction mixture was added with 100☐ of methanol and agitated for 1 hour to inactivate sodium borohydride. Then, pH of the reaction mixture was adjusted to 1.2 or less by adding concentrated hydrochloric acid, and agitated at 5° C. for 1 hour. The final reaction mixture was filtered under reduced pressure to remove crystals generated during the reaction. A filtrate thus obtained was concentrated under reduced pressure to obtain 89 g of crude 4-ethoxycarbonylamino-(S)-1,2-butandiol 5.

$^1$H-NMR (D$_2$O): δ 3.9-4.0 (m, 2H), 3.6-3.65 (m, 1H), 3.43-3.5 (m, 1H), 3.3-3.4 (1, 1H), 3.0-3.08 (m, 2H), 1.4-1.5 (m, 2H), 1.08 (t, 3H, J=6.9 Hz).

EXAMPLE 4

Preparation of 4-amino-(S)-1,2-butandiol bromate 6

After 4-ethoxycarbonylamino-(S)-1,2-butandiol 5 (0.564 mol, 100 g) and 48% HBr (285 g) were added to a 500☐ round-bottom flask and completely dissolved, the reaction mixture was agitated under reflux for 5 hours. After the completion of the reaction was confirmed, the resulting mixture was concentrated under reduced pressure to obtain 109 g of crude 4-amino-(S)-1,2-butandiol bromate 6.

$^1$H-NMR (D$_2$O): δ 3.62-3.68 (m, 1H), 3.3-3.5 (m, 2H), 2.9-3.1 (m, 2H), 1.5-1.8 (m, 2H).

EXAMPLE 5

Preparation of 4-amino-1-bromo-(S)-2-butanol bromate 7

4-Amino-(S)-1,2-butandiol bromate 6 (0.537 mol, 100 g) and an acetic acid solution (185 g) with 33% bromic acid dissolved therein were added to a 500☐ round-bottom flask and the mixture was agitated at 40° C. for 2 hours. After the preparation of an intermediate was confirmed by Thin Layer Chromatography (TLC), anhydrous ethanol (285 g) was added thereto. The reaction mixture was agitated under reflux for 3 hours to complete the reaction and then concentrated under reduced pressure to completely remove the solvent, thereby obtaining 115 g of crude 4-amino-1-bromo-(S)-2-butanol bromate 7.

$^1$H-NMR (D$_2$O): δ 3.97-4.02 (m, 1H), 3.45-3.51 (m, 2H), 3.43-3.5 (m, 1H), 3.15 (t, 2H, J=7.2 Hz), 1.86-2.01 (m, 2H).

EXAMPLE 6

Preparation of (S)-3-hydroxypyrrolidine 1

After 4-amino-1-bromo-(S)-2-butanol bromate 7 (2.001 mol, 500 g) and ethanol (1500☐) were added to a 3000☐ round-bottom flask and completely dissolved, potassium carbonate (555 g) was added thereto and the mixture was agitated under reflux for 4 hours to complete the reaction. After the completion of the reaction was confirmed, the reaction mixture was cooled down to room temperature, added with potassium hydroxide (250 g), and agitated again under reflux for 2 hours. After the reaction mixture solution was cooled down to room temperature, it was filtered under reduced pressure to remove generated salts. A filtrate thus obtained was concentrated under reduced pressure to obtain 170 g of crude (S)-3-hydroxypyrrolidine. The obtained compound was distillated under reduced pressure at conditions of 3 mmHg and 120° C. to obtain 127 g of pure (S)-3-hydroxypyrrolidine 1.

$^1$H-NMR (CDCl$_3$): δ 4.3-4.4 (m, 1H), 3.05-3.15 (m, 1H), 3.0 (bs, 2H), 2.75-2.9 (m, 3H), 1.85-2.0 (m, 1H), 1.6-1.75 (m, 1H).

EXAMPLE 7

Preparation of (S)-3-hydroxypyrrolidine 1

(S)-3-Hydroxypyrrolidine 1 could be prepared even when performing the reaction by using the same raw materials as Example 6 but adding 100 g of potassium hydroxide as a base.
*

EXAMPLE 8

Preparation of (S)-3-hydroxy-2-pyrrolidineon 9

After 4-amino-(S)-2-hydroxybutylic acid 2 (0.1 mol, 11.91 g) was dissolved in a solvent of methanol (1.5 mol, 48.06 g) contained in a 500☐ round-bottom flask, sulfuric acid (1 to 2 equivalents) was added thereto at 25° C. When 4-amino-(S)-2-hydroxybutylic acid 2 was completely dissolved, the reaction mixture was heated to 80° C. and agitated under reflux for 4 hours to complete the reaction. Thereafter, 4-amino-(S)-2-hydroxybutylic acid methylester sulfonate 8 was confirmed by NMR.

$^1$H-NMR (D$_2$O): δ 4.46 (dd, 1H, J=8.4 Hz, 4.2 Hz), 3.78 (s, 3H), 3.17 (t, 2H, J=7.2 Hz), 2.18-2.35 (m, 1H), 1.95-2.13 (m, 1H).

After the reaction mixture was cooled down to room temperature, water (11.91 g) and potassium carbonate were added thereto and agitated at room temperature for 12 hours to obtain (S)-3-hydroxy-2-pyrrolidineon. At this time, the formation of (S)-3-hydroxy-2-pyrrolidineon was confirmed by NMR. Inorganic substances, which were precipitated by adding methanol to a residue obtained after filtering and concentrating the reaction mixture, were removed by filtering the reaction mixture twice, and a filtrate thus obtained was concentrated under reduced pressure to obtain (S)-3-hydroxy-2-pyrrolidineon 9 (yield: 89%).

$^1$H-NMR (DMSO-d$_6$): δ 7.6 (bs, 1H), 5.4 (bs, 1H), 3.97 (t, 1H, J=8.4 Hz), 3.0-3.2 (m, 2H), 2.2-2.3 (m, 1H), 1.6-1.8 (m, 1H).

EXAMPLE 9

Preparation of (S)-3-hydroxypyrrolidine 1

(S)-3-Hydroxy-2-pyrrolidineon 9 (0.1 mol, 10.11 g), diglym (1.13 mol, 151.65 g) and NaBH$_4$ (0.4 mol, 15.13 g) were added to a 500☐ round-bottom flask at 25° C., and sulfuric acid (20.2 g) was gently dropped thereto for 1 hour. After the dropping, the mixture was heated to 80° C. and kept for 12 hours to complete the reaction. When the reaction was completed, methanol was added thereto to inactivate the reaction, and the reaction mixture was neutralized with diluted hydrochloric acid (0.4 mol, 41.67 g). Then, pH of the reaction mixture was adjusted to 11 or more by using an aqueous solution of sodium hydroxide (10N 35☐), and salts precipitated therefrom were removed through filtration. A resulting filtrate was concentrated under reduced pressure to obtain a (S)-3-hydroxypyrrolidine 1 residue. The residue was distilled under reduced pressure to obtain pure (S)-3-hydroxypyrrolidine 1.

$^1$H-NMR (CDCl$_3$): δ 4.3-4.4 (m, 1H), 3.05-3.15 (m, 1H), 3.0 (bs, 2H), 2.75-2.9 (m, 3H), 1.85-2.0 (m, 1H), 1.6-1.75 (m, 1H).

INDUSTRIAL APPLICABILITY

As described above, the present invention provides a method of economically and industrially preparing (S)-3-hydroxypyrrolidine, and preparing optically and chemically pure (S)-3-hydroxypyrrolidine through simple distillation under reduced pressure without an additional purification process during reaction. (S)-3-hydroxypyrrolidine thus prepared can be effectively used as a major raw material for preparation of various chiral pharmaceutical products, such as a major intermediate raw material of a calcium antagonist (Barnidipine), carbapenem antibiotics, quinolone-based antibiotics, analgesics, and a major intermediate raw material of a neurotransmitter, in a very wide industrial field.

The invention claimed is:

1. A method of preparing (S)-3-hydroxypyrrolidine, comprising the steps of:
    forming an amine protecting group in an amine group by using optically pure 4-amino-(S)-2-hydroxybutylic acid represented by the following Formula 2 as a starting material;
    reducing a carboxylic acid group to a primary alcohol;
    removing the amine protecting group to form an amine salt;
    halogenating the primary alcohol to perform activation into a leaving group; and
    synthesizing optically pure (S)-3-hydroxypyrrolidine represented by the following Formula 1 through amine cyclization:

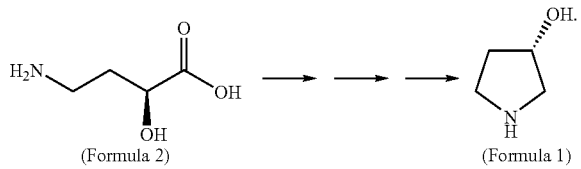

2. The method as claimed in claim 1, wherein a compound prepared in the step of forming the amine protecting group in the amine group of 4-amino-(S)-2-hydroxybutylic acid is a compound represented by the following Formula 3:

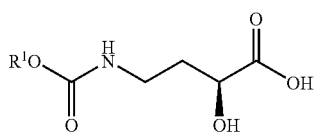

(Formula 3)

where $R^1$ is a $C_1$~$C_{12}$ linear or branched alkyl or benzyl group.

3. The method as claimed in claim 1, wherein the step of reducing the carboxylic acid group into the primary alcohol is performed by esterifying the carboxylic acid group into an ester compound represented by the following Formula 4 and reducing an ester group into the primary alcohol:

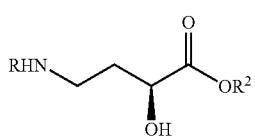

(Formula 4)

where R is an amine protecting group, and $R^2$ is a $C_1$~$C_{12}$ linear or branched alkyl or benzyl group.

4. The method as claimed in claim 1, wherein a compound prepared in the step of removing the amine protecting group to form the amine salt is a compound represented by the following Formula 5:

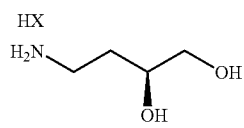

(Formula 5)

where HX is halogen acid or sulfuric acid.

5. The method as claimed in claim 1, wherein a compound prepared in the step of halogenating the primary alcohol to perform activation into the leaving group is a compound represented by the following Formula 6:

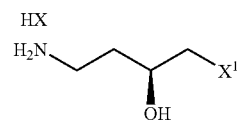

(Formula 6)

where HX is halogen acid or sulfuric acid, and $X^1$ is halogen.

6. The method as claimed in claim 1, wherein the step of forming the amine protecting group in the amine group of 4-amino-(S)-2-hydroxybutylic acid employs at least one reaction solvent selected from the group consisting of water, 1,4-dioxane, tetrahydrofuran and acetonitrile.

7. The method as claimed in claim 1, wherein the step of halogenating the primary alcohol to perform activation into the leaving group uses bromic acid and acetic acid, anhydride bromic acid or acetylbromide when the primary alcohol is brominated.

8. The method as claimed in claim 1, wherein the step of halogenating the primary alcohol to perform activation into a leaving group is performed at a reaction temperature ranging from 0 to 100° C. by using a $C_1$~$C_4$ liquid alkyl solvent with a carboxylic acid group as a reaction solvent.

9. The method as claimed in claim 1, wherein the step of synthesizing optically pure (S)-3-hydroxypyrrolidine through the amine cyclization is performed by using water, $C_1$~$C_4$ linear or branched alcohol, or a mixture thereof as a reaction solvent, and $Na_2CO_3$, $K_2CO_3$, $NaHCO_3$, LiOH, NaOH, KOH, $Ca(OH)_2$ or triethylamine as a base.

10. A method of preparing (S)-3-hydroxypyrrolidine, comprising the steps of:
    forming an ester compound by esterifying a carboxylic acid group of optically pure 4-amino-(S)-2-hydroxybutylic acid represented by the following Formula 2 used as a starting material;
    forming a lactam compound through lactam cyclization of the ester compound; and
    synthesizing optically pure (S)-3-hydroxypyrrolidine represented by the following Formula 1 through amide reduction of the lactam compound:

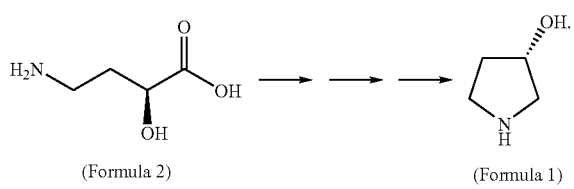

(Formula 2)     (Formula 1)

11. The method as claimed in claim 10, wherein the ester compound is a compound represented by the following Formula 7:

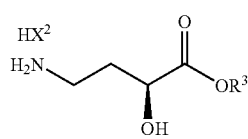

(Formula 7)

where $R^3$ is a $C_1$~$C_{12}$ linear or branched alkyl or benzyl group, and $HX^2$ is halogen acid or sulfuric acid.

12. The method as claimed in claim 10, wherein the step of preparing the ester compound by esterifying the carboxylic acid group of optically pure 4-amino-(S)-2-hydroxybutylic acid employs a base selected from the group consisting of sodium carbonate, potassium carbonate, sodium bicarbonate, potassium hydroxide, sodium hydroxide and a tertiary alcohol.

13. The method as claimed in claim 10, wherein the step of synthesizing optically pure (S)-3-hydroxypyrrolidine through the amide reduction of the lactam compound uses diglym as a reaction solvent.

14. The method as claimed in claim 13, wherein the step of synthesizing optically pure (S)-3-hydroxypyrrolidine through the amide reduction of the lactam compound is performed at a reaction temperature of 20 to 150° C. by using 1 to 10 equivalents of sodium borohydride as a reducing agent and 1 to 4 equivalents of sulfuric acid based on the lactam compound.

15. The method as claimed in claim 10, wherein the step of forming the ester compound by esterifying the carboxylic acid group of optically pure 4-amino-(S)-2-hydroxybutylic acid and the step of synthesizing optically pure (S)-3-hydroxypyrrolidine through the amide reduction of the lactam compound are performed in a consecutive manner.

* * * * *